US012465387B2

(12) United States Patent
Turano et al.

(10) Patent No.: US 12,465,387 B2
(45) Date of Patent: Nov. 11, 2025

(54) MICRODEBRIDER WITH IMPROVED CUTTING AND REDUCED CLOGGING

(71) Applicant: Medtronic Xomed, LLC, Minneapolis, MN (US)

(72) Inventors: Bo D. Turano, Jacksonville, FL (US); Phillip J. Berman, Jacksonville, FL (US)

(73) Assignee: Medtronic Xomed LLC, Minneapolis, MN (US)

( * ) Notice: Subject to any disclaimer, the term of this patent is extended or adjusted under 35 U.S.C. 154(b) by 377 days.

(21) Appl. No.: 17/900,389

(22) Filed: Aug. 31, 2022

(65) Prior Publication Data

US 2024/0065719 A1 Feb. 29, 2024

(51) Int. Cl.
*A61B 17/32* (2006.01)
*A61B 17/3207* (2006.01)

(52) U.S. Cl.
CPC .................. *A61B 17/32002* (2013.01); *A61B 17/320783* (2013.01); *A61B 2217/005* (2013.01); *A61B 2217/007* (2013.01)

(58) Field of Classification Search
CPC ...... A61B 17/32002; A61B 17/320783; A61B 2217/005; A61B 2217/007
See application file for complete search history.

(56) References Cited

U.S. PATENT DOCUMENTS 5,685,838 A 11/1997 Peters et al.
5,957,881 A 9/1999 Peters et al.
6,068,641 A * 5/2000 Varsseveld ....... A61B 17/32002 606/170
6,132,448 A * 10/2000 Perez .................. A46B 5/0087 606/180
6,293,957 B1 9/2001 Peters et al.
(Continued)

FOREIGN PATENT DOCUMENTS

EP 0669105 A2 8/1995

OTHER PUBLICATIONS

Extended European Search Report EP23193260.9 dated Apr. 9, 2024, 16pp.

(Continued)

*Primary Examiner* — Tan-Uyen T Ho
*Assistant Examiner* — Cherie M Poland
(74) *Attorney, Agent, or Firm* — Carter, DeLuca & Farrell LLP

(57) ABSTRACT

A device for removing tissue includes a housing having an outer tube extending therefrom including an axis defined therealong. A middle tube is supported within the outer tube having an opening at a distal end with an edge. The middle tube includes a swage proximate the area of engagement between the middle and outer tubes. An inner tube is disposed within the middle tube and includes an opening having teeth at a distal end in registration with the opening in the middle tube, the inner tube rotates relative to the middle tube and the teeth, and the edge cooperate to cut tissue. A lumen is defined through the inner tube and extends from the opening to a suction source. The swage of the middle tube and the increased inner diameter associated therewith allows the inner tube to maintain a constant inner diameter along a length thereof, reducing choke points along the lumen.

20 Claims, 5 Drawing Sheets

(56) References Cited

U.S. PATENT DOCUMENTS

| | | | |
|---|---|---|---|
| 6,645,218 B1 | 11/2003 | Cassidy et al. | |
| 6,824,552 B2 | 11/2004 | Robison et al. | |
| 7,077,845 B2 | 7/2006 | Hacker et al. | |
| 7,244,263 B2 | 7/2007 | Robison et al. | |
| 7,674,263 B2 | 3/2010 | Ryan | |
| 7,699,846 B2 | 4/2010 | Ryan | |
| 7,719,437 B2 | 5/2010 | Bertram, III | |
| 7,803,170 B2 | 9/2010 | Mitusina | |
| 7,854,736 B2 | 12/2010 | Ryan | |
| 7,942,880 B2 | 5/2011 | Bertram, III | |
| 7,993,360 B2 | 8/2011 | Hacker et al. | |
| 8,052,706 B2 | 11/2011 | Mitusina | |
| 8,057,500 B2 | 11/2011 | Mitusina | |
| 8,142,464 B2 | 3/2012 | Mitusina | |
| 8,366,559 B2 | 2/2013 | Papenfuss et al. | |
| 8,808,375 B2 | 8/2014 | Bertram, III | |
| 8,852,191 B2 | 10/2014 | Bertram, III | |
| 8,870,893 B2 | 10/2014 | Makower et al. | |
| 8,944,926 B2 | 2/2015 | Kramer et al. | |
| 9,198,685 B2 | 12/2015 | Edwards et al. | |
| 9,381,032 B2 | 7/2016 | Edwards et al. | |
| 9,474,541 B2 | 10/2016 | Zider et al. | |
| 9,486,232 B2 | 11/2016 | Heisler et al. | |
| 9,517,076 B2 | 12/2016 | Papenfuss | |
| 9,603,607 B2 | 3/2017 | Papenfuss | |
| 9,668,751 B2 | 6/2017 | Papenfuss | |
| 9,775,967 B2 | 10/2017 | Hatta et al. | |
| 9,808,867 B2 | 11/2017 | Krause et al. | |
| 9,833,249 B2 | 12/2017 | Bertram, III | |
| 9,839,441 B2 | 12/2017 | Hayes et al. | |
| 10,179,002 B2 | 1/2019 | Wasicek et al. | |
| 10,271,830 B2 | 4/2019 | Papenfuss et al. | |
| 10,492,800 B2 | 12/2019 | Papenfuss | |
| 10,524,820 B2 | 1/2020 | Algawi et al. | |
| 10,743,912 B2 | 8/2020 | Papenfuss | |
| 10,779,806 B2 | 9/2020 | Kieturakis et al. | |
| 11,020,139 B2 | 6/2021 | Curtin et al. | |
| 11,064,980 B2 | 7/2021 | Papenfuss et al. | |
| 11,065,012 B2 | 7/2021 | Edwards | |
| 2009/0270812 A1* | 10/2009 | Litscher | A61B 17/42 604/164.01 |
| 2011/0224577 A1 | 9/2011 | Park | |
| 2011/0313326 A1 | 12/2011 | Johansen | |
| 2015/0327880 A1 | 11/2015 | Wasicek et al. | |
| 2015/0327881 A1 | 11/2015 | Willhite et al. | |
| 2019/0038305 A1* | 2/2019 | Smith | A61B 17/1659 |
| 2019/0357924 A1 | 11/2019 | Papenfuss | |
| 2021/0282799 A1* | 9/2021 | Curtin | A61B 17/32002 |
| 2022/0133360 A1 | 5/2022 | Papenfuss et al. | |

OTHER PUBLICATIONS

Partial European Search Report EP23193260.9 dated Jan. 15, 2024, 15pp.

* cited by examiner

MICRODEBRIDER WITH IMPROVED CUTTING AND REDUCED CLOGGING

FIELD

The present disclosure is generally directed to devices and systems for cutting and treating tissue such as bone and soft tissue. The devices and systems of the present disclosure may be particularly suitable for sinus applications and nasopharyngeal/laryngeal procedures.

BACKGROUND

Devices and systems in accordance with the present disclosure may be suitable for a variety of procedures including ear, nose and throat (ENT) procedures, head and neck procedures, otology procedures, including otoneurologic procedures. Other surgical procedures suitable for use with the devices described herein include: mastoidectomies; nasopharyngeal and laryngeal procedures such as tonsillectomies, tracheal procedures, adenoidectomies, laryngeal lesion removal, and polypectomies; for sinus procedures such as polypectomies, septoplasties, removals of septal spurs, antrostomies, frontal sinus opening, endoscopic DCR, correction of deviated septums and trans-sphenoidal procedures; rhinoplasty and removal of fatty tissue in the maxillary and mandibular regions of the face.

Of particular significance is the usefulness of the devices and systems described herein with sinus surgery which is often challenging due to the obvious location of the sinus cavity to sensitive organs such as the eyes and brain. Moreover, the relatively small size of the anatomy of interest to the surgeon and the complexity of the typical procedures places a heavy emphasis on precision. Examples of debriders with mechanical cutting components are described in commonly-owned U.S. Pat. Nos. 5,685,838; 5,957,881; and 6,293,957, the entire contents of each of which being incorporated by reference herein.

The Medtronic Straightshot® RAD40 or RAD60 Microdebriders use sharp cutters to cut tissue, and suction to withdraw tissue. While tissue debridement with the Medtronic microdebrider systems is a simple and safe technique, the blade geometry of these devices during rotation tend to push the tissue distally during rotation rather than proximally typically requiring additional suction to force the tissue into the instrument. Other areas of the distal end of the device tend to cause tissue build-up or so-called choke points around the distal junction between the middle and outer tubes leading to clogging requiring surgeon intervention.

SUMMARY

Provided in accordance with the present disclosure is a device for removing tissue which includes a housing having an outer tube extending therefrom and a longitudinal axis defined therealong. A middle tube is operably supported concentrically within the outer tube by a bushing and is configured to extend from a distal end thereof. The middle tube includes an opening defined at a distal end thereof having an edge on one or both sides of the opening, and a swaged portion defined therein configured to increase the inside diameter of the middle tube proximate the area of operative engagement between the middle tube and the outer tube.

An inner tube is concentrically disposed within the middle tube and includes an opening having a series of teeth at a distal end thereof in longitudinal registration with the opening in the middle tube. The inner tube is adapted to couple to a power source such that, upon activation thereof, the inner tube rotates relative to the middle tube and the series of teeth, and the edges cooperate to cut tissue or bone disposed therebetween. The inner tube defines a lumen therethrough that extends therealong from the opening, and a portion of the lumen is adapted to connect to a suction source. The swaged portion of the middle tube and the increased diameter associated therewith allows the inner tube to maintain a constant inner diameter along a substantial length thereof reducing potential choke points along the lumen to the suction source.

In aspects according to the present disclosure, a channel is defined between the concentric inner and middle tubes along a length thereof for passing a fluid therealong. In other aspects according to the present disclosure, the fluid is passed distally through the channel into the openings in respective inner and middle tubes.

In aspects according to the present disclosure, the channel is adapted to connect to a fluid source. In other aspects according to the present disclosure, the fluid is saline.

In aspects according to the present disclosure, the edge on the one or both sides of the opening of the middle tube includes a series of teeth.

In aspects according to the present disclosure, the opening of the middle tube includes an edge defined therearound, the edge including a series of teeth configured to cooperate with the series of teeth of the inner tube to cut tissue or bone during rotation thereof.

In aspects according to the present disclosure, the proximal-to-distal, peak-to-peak alignment of the series of teeth of the inner tube is angled away from the longitudinal axis to draw tissue proximally into the lumen and therealong toward the suction source when the inner tube rotates in one of a clock-wise or counter-clockwise to cut tissue or bone.

In aspects according to the present disclosure, the proximal-to-distal, peak-to-peak alignment of the series of teeth of the middle tube is angled towards the longitudinal axis to draw tissue proximally into the lumen and therealong toward the suction source when the inner tube rotates in one of a clock-wise or counter-clockwise direction to cut tissue or bone.

Provided in accordance with the present disclosure is a device for removing tissue which includes a housing having an outer tube extending therefrom and a longitudinal axis defined therealong. A middle tube is operably supported concentrically within the outer tube and is configured to extend from a distal end thereof, the middle tube including an opening defined at a distal end thereof having an edge on one or both sides thereof.

An inner tube is concentrically disposed within the middle tube and includes an opening having a series of teeth at a distal end thereof in longitudinal registration with the opening in the middle tube. The inner tube is adapted to couple to a power source such that, upon activation thereof, the inner tube rotates relative to the middle tube and the series of teeth, and the edge cooperate to cut tissue or bone disposed therebetween. The inner tube defines a lumen therethrough that extends therealong from the opening, and a portion of the lumen is adapted to connect to a suction source. The proximal-to-distal, peak-to-peak alignment of the series of teeth of the inner tube is angled away from the longitudinal axis to draw tissue proximally into the lumen and therealong toward the suction source when the inner tube rotates in one of a clock-wise or counter-clockwise direction to cut tissue or bone.

In aspects according to the present disclosure, the edge on the one or both sides of the opening of the middle tube includes a series of teeth.

In aspects according to the present disclosure, the opening of the middle tube includes an edge defined therearound, the edge including a series of teeth configured to cooperate with the series of teeth of the inner tube to cut tissue or bone during rotation thereof. In other aspects according to the present disclosure, the proximal-to-distal, peak-to-peak alignment of the series of teeth of the middle tube is angled towards the longitudinal axis to draw tissue proximally into the lumen and therealong toward the suction source when the inner tube rotates in one of a clock-wise or counter-clockwise direction to cut tissue or bone.

In aspects according to the present disclosure, a channel is defined between the concentric inner and middle tubes along a length thereof for passing a fluid therealong. In other aspects according to the present disclosure, the fluid is passed distally through the channel into the openings in respective inner and middle tubes. In still other aspects according to the present disclosure, the channel is adapted to connect to a fluid source. In yet other aspects according to the present disclosure, the fluid is saline.

BRIEF DESCRIPTION OF THE DRAWINGS

In the drawings, where like numerals refer to like components throughout several views.

DETAILED DESCRIPTION

Figure 1:
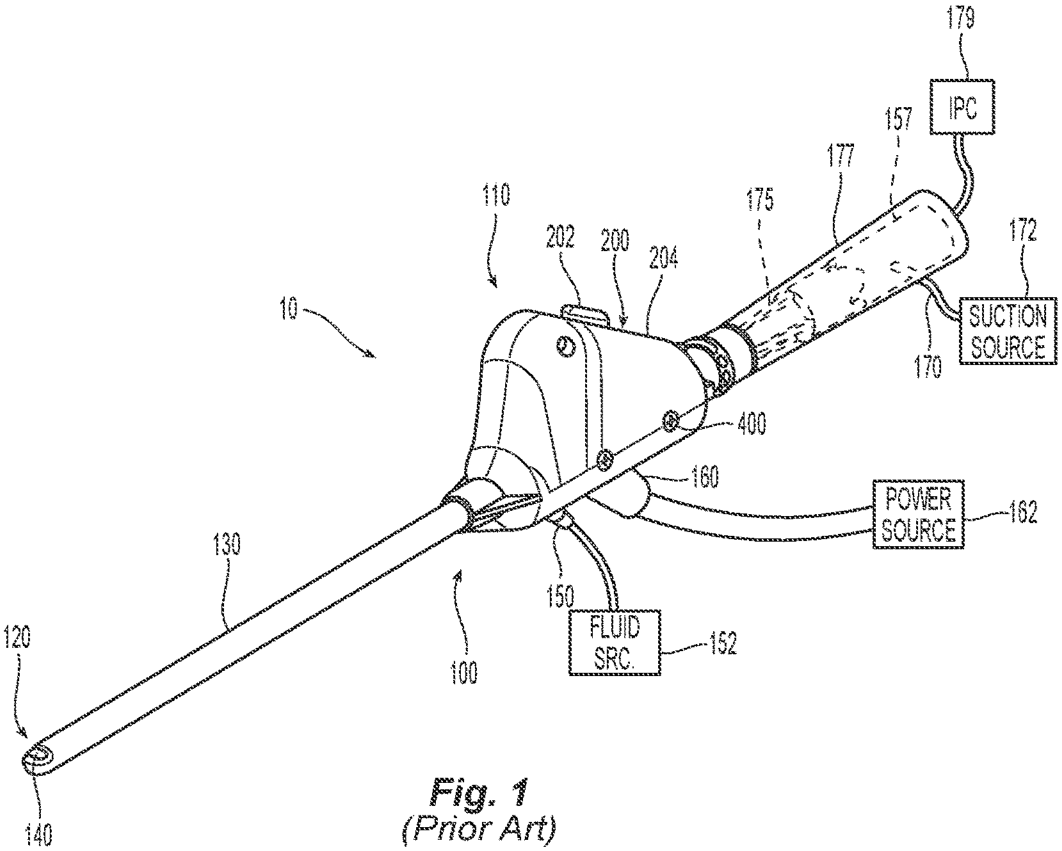
Fig. 1 (Prior Art)
FIG. 1 is a perspective view of a prior art system for performing one or more ENT surgical procedures.

FIG. 1 illustrates a prior art system 10 having a surgical device 100 including a distal end region indicated generally at 120 and a proximal end region indicated generally at 110. The device 100 includes an outer shaft 130 and an inner shaft 140 coaxially maintained within the outer shaft 130. A portion of the inner shaft 140 is shown in FIG. 1 at distal end region 120. Proximal end region 110 includes a button activation cell 200 having a housing 204 and an activation button 202, the proximal end region further including a hub 175 coupled to inner shaft 140. The hub 175 is configured to operably couple to a handpiece 177 which can be manipulated by a user (e.g., a surgeon). The handpiece 177, in turn, may be coupled to an integrated power console or IPC 179 for driving the device 100 and, specifically, for controlling rotation of inner shaft 140. The IPC 179 may also include a fluid source (not shown) for providing fluid to device 100.

Proximal end region 110 also includes a fluid source connector 150, a power source connector 160 and a suction source connector 170 operably connected to a fluid source 152, a power source 162, and a suction source 172, respectively, of system 10. While saline is particularly useful with the present disclosure, other fluids are contemplated. Power source 162, e.g., a generator, is an optional component of the system 10 and may be designed for use with bipolar energy. For example, the Transcollation® sealing energy supplied by the Aquamantys® System may be used. Both the fluid source 152 and suction source 172 are also optional components of system 10. However, use of fluid in conjunction with energy delivery may provide additional tissue benefits.

In use, a fluid (e.g., saline) may be emitted from an opening at the distal end region of the device 100. Tissue fragments and fluids can be removed from a surgical site through an opening (not shown in FIG. 1) in the distal end region via the suction source 172, as will be further explained below.

Figure 2:
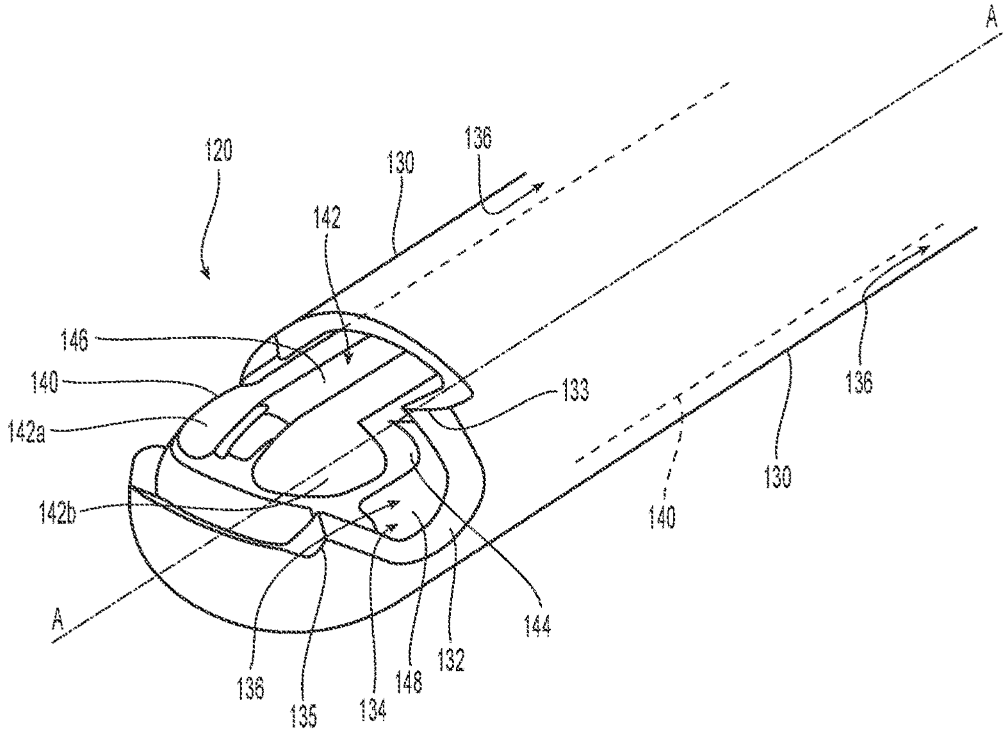
Fig. 2 (Prior Art)
FIG. 2 is an enlarged, perspective view of a distal end of a device for use with the system of FIG. 1.
Figure 3:
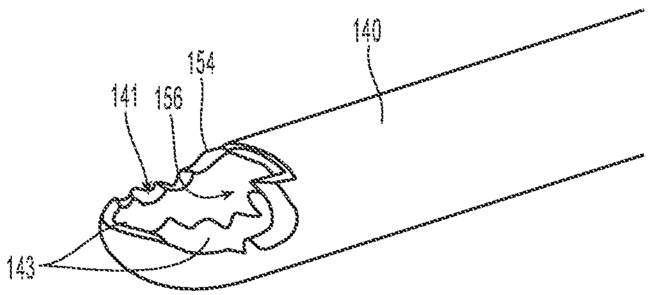
Fig. 3 (Prior Art)
FIG. 3 is an enlarged, perspective view of a distal end of another device for use with the system of FIG. 1.

FIG. 2 shows an enlarged perspective view of distal end portion 120 of device 100. The outer shaft 130 includes an opening 134 at a distal end 135 of the outer shaft 135. Opening 134 is defined by an outer shaft cutting edge or cutter 132, which includes cutting teeth 133. The outer shaft 130 may be rigid or malleable (or combinations thereof) and may be made of a variety of metals and/or polymers or combinations thereof, e.g., stainless steel. A distal portion 148 of the inner shaft 140 can be seen through the opening 134 of outer shaft 130. In FIG. 1, inner shaft 140 is depicted in a position such that an inner shaft or cutter 141 (FIG. 3), including cutting teeth 143 is facing an inner wall (not shown) of outer shaft 130. Cutter 141 defines an inner shaft opening 154 (FIG. 3). Outer and inner shaft cutters 132 and 141 may move relative to one another in oscillation or rotation (or both) in order to mechanically cut tissue. For example, outer shaft cutter 132 may remain stationary relative to the hub 175 while the inner shaft cutter 141 may rotate about a longitudinal axis A-A defined through the device 100 (FIG. 2), thereby cutting tissue.

Rotation of inner shaft 140 may be achieved via manipulation of hub 175 (FIG. 1) that can orient the inner shaft 140 relative to the outer shaft 130 and may additionally allow for locking of the inner shaft 140 relative to the outer shaft 130 in a desired position, i.e., inner shaft 140 may be locked in position when cutter 141 is facing down and an electrode assembly 142 is facing up. As described above, hub 175 may be connected to a handpiece 177 which may be controlled by an IPC 179. Alternatively, the hub 175 and/or handpiece 177 may be manipulated manually.

Inner shaft 140 may be selectively rotated to expose electrode assembly 142 including electrodes 142_a_, 142_b_, through opening 134 of outer shaft 130, as shown in FIG. 2. As depicted in FIG. 2, inner shaft 140 is positioned such that the inner shaft cutter 141 is facing the interior (not shown) of outer shaft 130 and may be in a downward facing direction and include a downward position. In the downward position, tissue is shielded from the inner shaft cutter 141 during hemostasis (via energy delivery through electrodes 142_a_, 142_b_), thereby delivering energy to tissue with no attendant risk that the cutting teeth 143 of the inner shaft 140 will diminish the efforts to achieve hemostasis. Device 100 may thus include two modes: a cutting or debridement mode and a sealing or hemostasis mode and the two modes may be mutually exclusive, i.e., hemostasis is achieved via energy delivery to tissue while cutters 132, 141 are not active or cutting. As described below, energy may be advantageously delivered simultaneously with a fluid such as saline to achieve an optimal tissue effect by delivering controlled RF energy to tissue.

As depicted in FIG. 3, when the inner shaft 140 is oriented such that cutter 141 is in the downward position, rotating inner shaft 140 approximately 180 degrees relative to the outer shaft 130 will expose inner shaft cutter 141 and inner shaft opening 154 through the outer shaft opening 134. When the inner shaft cutter 141 is positioned as shown in FIG. 3, the inner shaft cutter 141 may be in an upward position. The inner shaft opening 154 is fluidly connected to an inner shaft lumen 156 that extends from the inner shaft distal portion 148 to the proximal end 151 of inner shaft 140 and may be fluidly connected with the suction source 172. With this configuration, tissue cut via inner and outer shaft cutters 141, 132 may be aspirated into the inner shaft lumen 156 through the inner shaft opening 154 upon application of suction source 172, thereby removing tissue from a target site.

Figure 4:
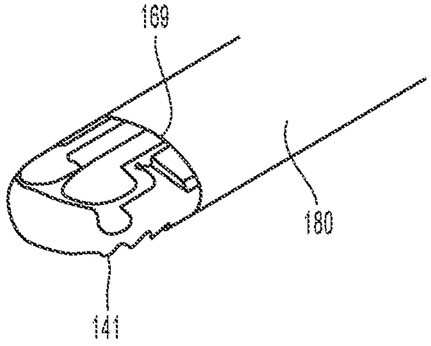
Fig. 4 (Prior Art)
FIGS. 4 and 5 are enlarged, perspective views of distal ends of a device for use with the system of FIG. 1.
Figure 5:
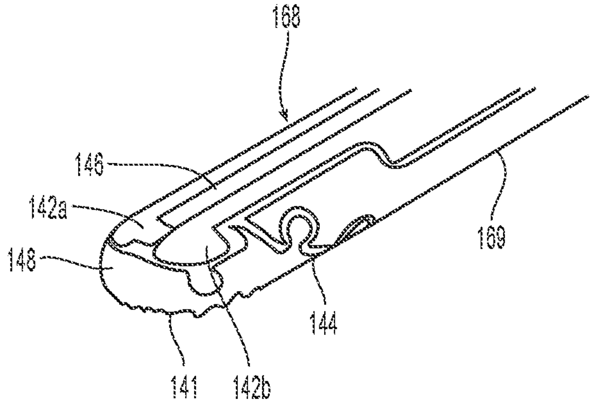
Fig. 5 (Prior Art)

With reference between FIGS. 4 and 5, the inner shaft 140 includes a proximal assembly 168 including a proximal assembly shaft component 169 (more clearly seen in FIG. 5) and electrodes 142*a* and 142*h*. Electrodes 142*a* and 142*b* may be used to deliver any suitable energy for purposes of coagulation, hemostasis or sealing of tissue. Electrodes 142*a* and 142*h* are particularly useful with fluid such as saline provided by fluid source 152 (FIG. 1) which may be emitted near the outer shaft opening 134. Outer shaft opening 134 is fluidly connected to an outer shaft lumen 136 that extends from outer shaft opening 134 to the proximal end region 110 of device 100 and may be fluidly connected to the fluid source 152 (FIG. 1). Thus, fluid can be delivered to the opening 134 of outer shaft 130 and interacts with electrode 142*a*, 142*b*.

Figure 6:
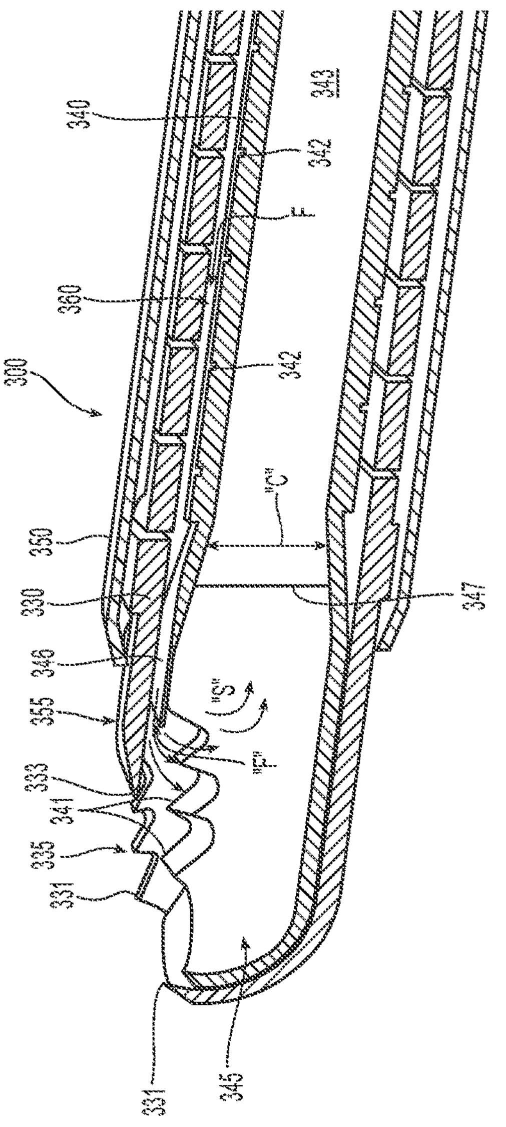
FIG. 6 is an enlarged, perspective view of a distal end of a device for use with the system of FIG. 1 including an inner tube, middle tube and an outer tube.

Turning to FIG. 6 which shows a cross-section of a distal end of another prior art surgical device 300 for use with various ENT procedures. Once example of such an device is sold by Medtronic under the tradename Straightshot® M4 RAD40 which enables a surgeon to perform procedures such as transnasal endoscopic bone and tumor removal under navigation utilizing irrigation and suction to help maximize visibility during surgery. Similar to the above-described device 100, the RAD 40 device 300 connects to Straightshot® M4 and enables a surgeon to rapidly shave bone or tissue without thermal burn by rotating the distal cutting teeth 341 of the inner tube 340 relative to the distal cutting teeth 331 of a middle tube 330 disposed within an outer tube 350. Irrigation fluid "F", e.g., saline, is supplied from a fluid source 152 between the channel 360 defined between the inner diameter of middle tube 330 and the outer diameter of inner tube 340 and to respective openings 335 and 345 thereof such that upon rotation of the inner tube 340 relative to the middle tube 330, the cooperating teeth, e.g., teeth 331 and teeth 341, shave bone or tissue disposed within the laterally-disposed windows while suction from the suction source 172 draws the debris through the inner lumen 343 defined within the device 300.

A distal portion 346 of the inner tube 340 includes an outer diameter sized to securely engage the inner tube 340 within the middle tube 330 (friction-fit) and includes a reduced diameter or neck 347 to facilitate fluid "F" flow through the channel 360 between the tubes 330 and 340. The reduced diameter neck 347 tends to create a choke point "C" for debris being suctioned through the lumen 343 which may require manual intervention by a surgeon during surgery.

Figure 7:
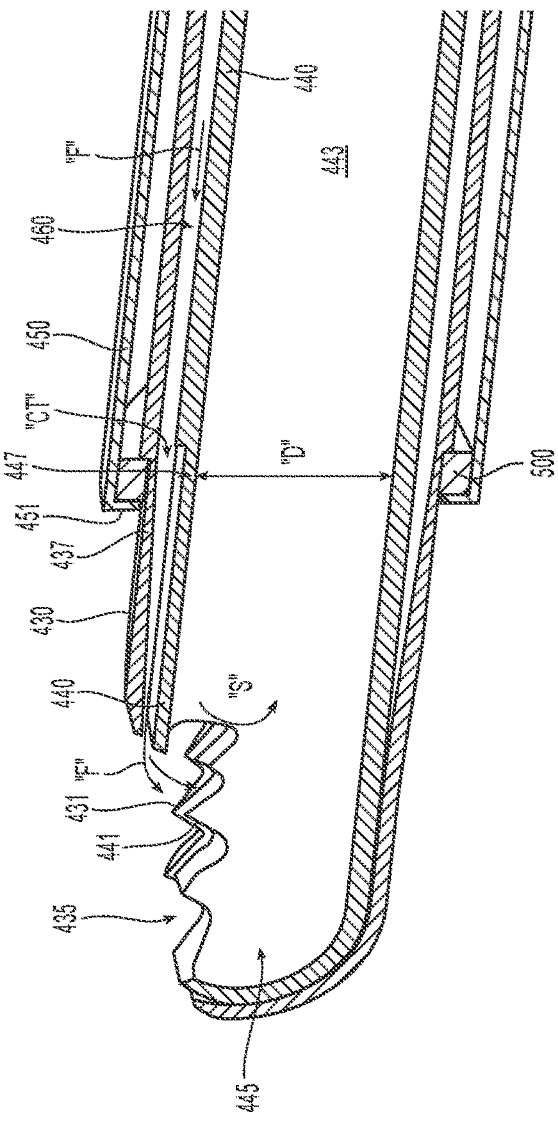
FIG. 7 is an enlarged, perspective view of a distal end of a device for use with the system of FIG. 1 according to the present disclosure including an inner tube, middle tube and an outer tube, the inner tube including a constant diameter to reduce potential debris choke points along the device suction path.

Turning to FIG. 7 which shows one embodiment of the presently disclosed microdebrider 400 which is similar to the above described device 300 but includes a constant diameter inner tube 440 which is configured to reduce the chances of debris clogging. Microdebrider 400 operates in a similar fashion to device 300 and includes similar elements thereto and, as such, only those elements that are different are described in further detail below. Microdebrider 400 is configured to operably connect to one or more devices for shaving tissue and bone, e.g., the Straightshot® M4 described above, and is configured to and shave tissue and bone in a rapid fashion as the inner tube 440 rotates at a high-speed relative to a middle tube 430. Fluid "F" from irrigation source 152 irrigates the tissue site from channel 460 defined between tubes 430, 440 and extending therealong into openings 435, 445 and shaved debris excised from the rotating teeth 431, 441 of respective tubes 430, 440 is drawn into lumen 443 of inner tube 443 via suction source 172 along path "S".

As mentioned above the inner tube 440 includes a constant diameter "D" as it extends therealong. The middle tube 430 is swaged (inner diameter is increased) at a point 437 proximate a distal end 451 of the outer tube 450 to accommodate for the constant diameter "D" of the inner tube 440. As a result, the inner tube 440 diameter allows a larger cutting area for removing tissue and bone. In embodiments, the inner diameter of the inner tube 440 and the "bite" of the teeth may increase as much as 27% (or larger) over prior art designs. The inner diameter 440 may be configured to maximize "bite" and minimize clogging by maintaining the inner diameter constant and increasing "bite" within the range of about 10% to about 30% depending upon a particular purpose or to achieve a particular result, e.g., depending on the type of tissue or bone being removed during surgery. Put differently, the cross-sectional area of the inner tube 440 may be increased up to about 85% over a swaged middle tube 430 design significantly enhancing tissue cutting and removal.

A bushing 500 is utilized to secure the middle tube 430 within the outer tube 450. Since the diameter "D" remains constant along suction path "S", e.g., there are no tissue choke points, the risk of tissue and/or bone debris clogging in the inner lumen 443 is reduced.

Figure 8A:
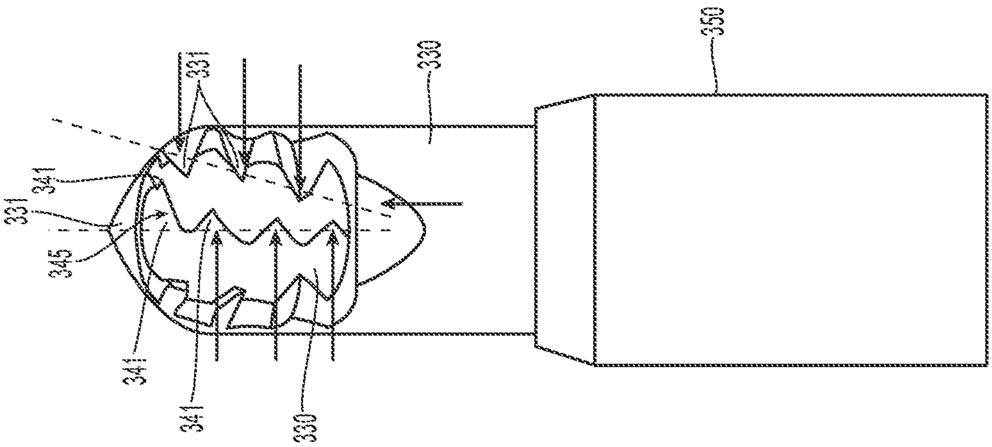
FIGS. 8A and 8B are enlarged, top views of the distal ends of a prior art device of FIG. 6 and the embodiment of FIG. 7, respectively, detailing the difference in peak-to-peak teeth alignment for directing tissue direction during excision.
Figure 8B:
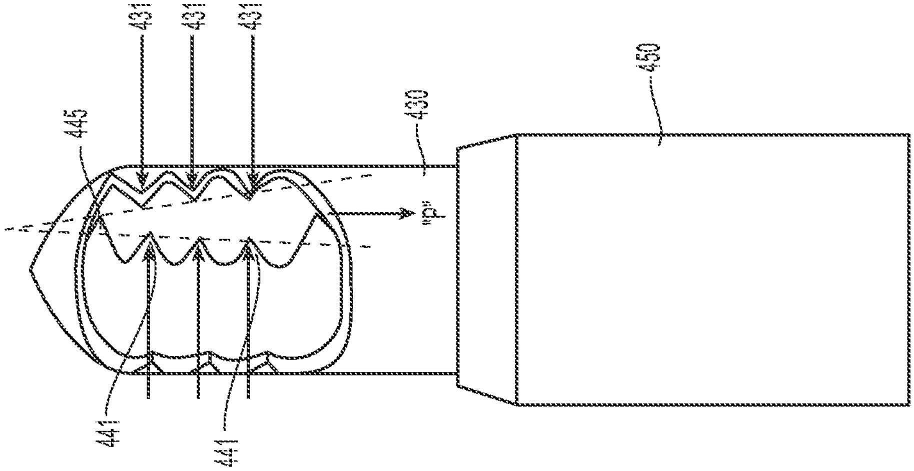

FIGS. 8A and 8B show top views of FIGS. 6 and 7, respectively, wherein the peak-to-peak alignment of the respective teeth of the device 300, e.g., teeth 331, 341 and the microdebrider device 400, e.g., teeth 431, 441, are shown by comparison. More particularly, the device 300 is configured to include a peak-to-peak teeth alignment (or sometimes referred to as peak-to-valley alignment) wherein the distal teeth 341 of the inner tube 340 are offset with respect to the proximal teeth 341 of the inner tube 340 relative to the middle tube 330 to form a V-shaped wedge (proximally-to-distally expanding V). As such, during rotation in the clockwise direction tissue and bone are spun distally "D" into the window 345 in the opposite direction of suction path "S" (FIG. 6), i.e., against the suction source 172.

FIG. 8B, on the other hand, depicts the design of the present disclosure which includes a peak-to-peak teeth alignment wherein the proximal teeth 441 of the inner tube 440 are offset with respect to the distal teeth 441 of the inner tube 440 relative to the middle to the teeth 431 of the middle tube 430 to form an inverted V-shaped wedge (distally-to-proximally expanding V). During rotation in the clockwise direction tissue and bone are spun proximally "P" into the opening 445 in the same direction of suction path "S" (FIG. 7). In other words, the teeth 431, 441 and the suction source 172 cooperate to excise and eliminate the shaved tissue and bone in a more efficient manner by virtue of the peak-to-peak teeth 441, 441 drawing tissue proximally along the suction path "S". More simply, proximal-to-distal, the peak-to-peak arrangement of the inner tube 440 may be angled away from the longitudinal axis A-A defined through the inner tube 440 or the proximal-to-distal, peak-to-peak arrangement of the middle tube 430 may be angled towards the longitudinal axis A-A defined through the inner tube 440. In either instance, these designs may also encourage drawing tissue proximally into the lumen 443 and along suction path "S". Although mentioned herein as "clockwise" direction, the instrument may be configured to rotate in a counter-clockwise direction in a similar fashion to draw tissue proximally along the suction path "S".

One of the advantages when using certain microdebriders, e.g., the Medtronic Straightshot® M4 (or M5), (hereinafter microdebrider 700 shown in FIG. 9), is the ability to rotate the inner tube 440 relative to the middle tube 430 three-hundred sixty degrees (3601 to excise tissue and bone without rotating the outer tube 450. This gives a surgeon a wide degree of flexibility when using a Navigation system, e.g., the Medtronic Fusion® ENT Navigation system (hereinafter system 600), in that any number of devices 400 having varying angles alpha "α" (FIG. 9) can be attached to the microdebrider 700 and tissue or bone can be easily excised.

Figure 9:
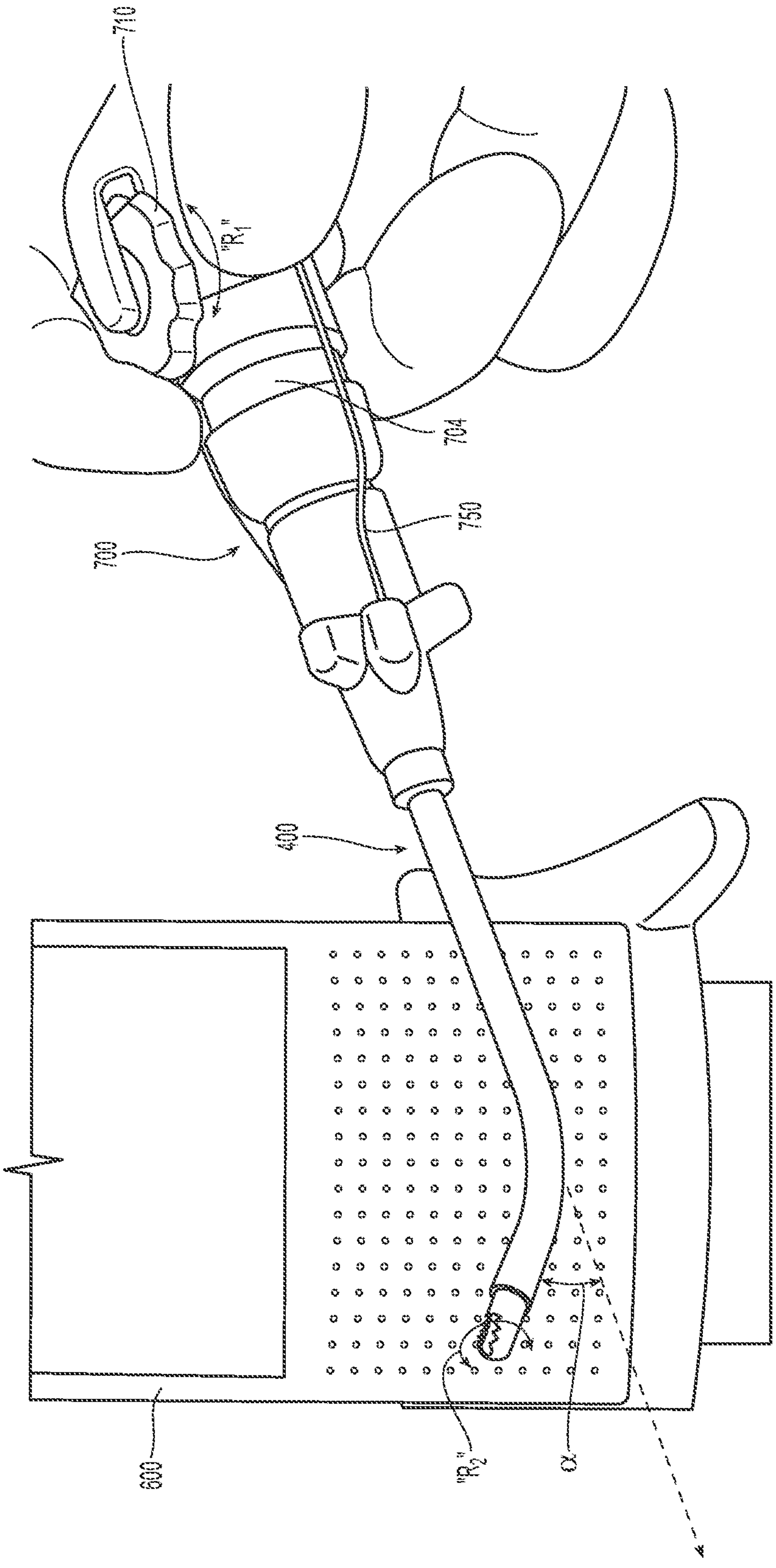
FIG. 9 is a side, perspective view of the device of FIG. 6 shown assembled on a tissue removal system and being used in conjunction with a surgical navigation system.

More particularly and with particular reference to FIG. 9, microdebrider 700 may be configured to operably engage device 400 having inner tube 440, middle tube 430 and outer tube 450 and attach to an irrigation source 750 and a suction source 172 (FIG. 1) as described above. A rotation wheel 710 is disposed atop the housing 704 and configured to operably communicate with the middle tube 430 and is selectively rotatable in direction "$R_1$" to permit 360° of selective rotation in direction "$R_1$" of the cutting window between openings 445, 435 of the inner and middle tubes 440, 430, respectively, without requiring reorientation of the microdebrider 700 in situ. In some embodiments, the rotation wheel 710 may be operably coupled to the middle tube 430.

The combination of the surgeon being able to initially determine the most efficient angle α for the device 400 at the onset of the surgery (or selectively switch devices 400 as needed during surgery), the ability of the surgeon to rotate the cutting window between the inner and middle tubes 440, 430 with the rotation wheel 710 without reorientation of the device 400 in situ, and the use of the navigation system 600, all enhance the surgeon's ability to perform the overall surgical procedure.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular configurations. Those skilled in the art will envision other modifications within the scope and spirit of the claims appended hereto.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended hereto.

What is claimed is:

1. A device for removing tissue, comprising:

a housing having an outer tube extending therefrom including a longitudinal axis defined therealong;

a middle tube operably supported concentrically within the outer tube by a bushing and configured to extend from a distal end thereof, the middle tube including an opening defined at the distal end thereof having an edge on at least one side thereof, the middle tube including a swaged portion defined therein extending proximally relative to a distal end of the opening, the swaged portion configured to increase the inside diameter of the middle tube proximate the area of operative engagement between the middle tube and the outer tube; and an inner tube concentrically disposed within the middle tube including an opening having a series of teeth at a distal end thereof in longitudinal registration with the opening in the middle tube, the inner tube adapted to couple to a power source such that, upon activation thereof, the inner tube rotates relative to the middle tube and the series of teeth and the edge of the middle tube cooperate to cut tissue or bone disposed therebetween, the inner tube defining a lumen therethrough and extending therealong from the opening, a portion of the lumen adapted to connect to a suction source, wherein the swaged portion of the middle tube and the increased diameter associated therewith allows the inner tube to maintain a constant inner diameter along a length thereof reducing potential choke points along the lumen to the suction source.

2. The device for removing tissue according to claim 1, wherein a channel is defined between the concentric inner and middle tubes along a length thereof for passing a fluid therealong.

3. The device for removing tissue according to claim 2, wherein the fluid is passed distally through the channel into the openings in respective inner and middle tubes.

4. The device for removing tissue according to claim 2, wherein the channel is adapted to connect to a fluid source.

5. The device for removing tissue according to claim 2, wherein the fluid is saline.

6. The device for removing tissue according to claim 1, wherein the edge on the at least one side of the opening of the middle tube includes a series of teeth.

7. The device for removing tissue according to claim 1, wherein the opening of the middle tube includes an edge defined therearound, the edge including a series of teeth configured to cooperate with the series of teeth of the inner tube to cut tissue or bone during rotation thereof.

8. The device for removing tissue according to claim 7, wherein the proximal-to-distal, peak-to-peak alignment of the series of teeth of the inner tube is angled away from the longitudinal axis to draw tissue proximally into the lumen and therealong toward the suction source when the inner tube rotates in one of a clock-wise or counter-clockwise direction to cut tissue or bone.

9. The device for removing tissue according to claim 7, wherein the proximal-to-distal, peak-to-peak alignment of the series of teeth of the middle tube is angled towards the longitudinal axis to draw tissue proximally into the lumen and therealong toward the suction source when the inner tube rotates in one of a clock-wise or counter-clockwise direction to cut tissue or bone.

10. The device for removing tissue according to claim 9, wherein the proximal-to-distal, peak-to-peak alignment of the series of teeth of the inner tube is angled away from the longitudinal axis to draw tissue proximally into the lumen and therealong toward the suction source when the inner tube rotates in one of a clock-wise or counter-clockwise direction to cut tissue or bone.

11. The device for removing tissue according to claim 1, wherein the increased inner diameter of the middle tube is configured to accommodate an inner tube with larger inner diameter contributing to the reduction of potential choke points along the lumen to the suction source.

12. The device for removing tissue according to claim 1, wherein the series of teeth is arranged in proximal-to-distal, peak-to-peak alignment, the series of teeth being angled away from the longitudinal axis to draw tissue proximally into and along a lumen defined through the inner tube toward the suction source when the inner tube rotates in one of a clock-wise or counter-clockwise direction to cut tissue or bone.

13. A device for removing tissue, comprising:

a housing having an outer tube extending therefrom along a longitudinal axis defined therealong;

a middle tube operably supported concentrically within the outer tube and configured to extend from a distal end thereof, the middle tube including an opening defined at a distal end thereof having an edge on at least one side thereof; and an inner tube concentrically disposed within the middle tube including an opening having a series of teeth at a distal end thereof in longitudinal registration with the opening in the middle tube, the inner tube adapted to couple to a power source such that, upon activation thereof, the inner tube rotates relative to the middle tube and the series of teeth and the edge cooperate to cut tissue or bone disposed therebetween, the inner tube defining a lumen therethrough and extending therealong from the opening, a portion of the lumen adapted to connect to a suction source, wherein the proximal-to-distal, peak-to-peak alignment of the series of teeth of the inner tube is angled away from the longitudinal axis to draw tissue proximally into the lumen and therealong toward the suction source when the inner tube rotates in one of a clock-wise or counter-clockwise direction to cut tissue or bone.

14. The device for removing tissue according to claim 13, wherein the edge on the at least one side of the opening of the middle tube includes a series of teeth.

15. The device for removing tissue according to claim 13, wherein the opening of the middle tube includes an edge defined therearound, the edge including a series of teeth configured to cooperate with the series of teeth of the inner tube to cut tissue or bone during rotation thereof.

16. The device for removing tissue according to claim 15, wherein the proximal-to-distal, peak-to-peak alignment of the series of teeth of the middle tube is angled towards the longitudinal axis to draw tissue proximally into the lumen and therealong toward the suction source when the inner tube rotates in one of a clock-wise or counter-clockwise direction to cut tissue or bone.

17. The device for removing tissue according to claim 13, wherein a channel is defined between the concentric inner and middle tubes along a length thereof for passing a fluid therealong.

18. The device for removing tissue according to claim 17, wherein the fluid is passed distally through the channel into the openings in respective inner and middle tubes.

19. The device for removing tissue according to claim 17, wherein the channel is adapted to connect to a fluid source.

20. The device for removing tissue according to claim 17, wherein the fluid is saline.

* * * * *